(12) United States Patent
Mitchell

(10) Patent No.: US 7,833,246 B2
(45) Date of Patent: Nov. 16, 2010

(54) INTERSPINOUS PROCESS AND SACRUM IMPLANT AND METHOD

(75) Inventor: Steve Mitchell, Pleasant Hill, CA (US)

(73) Assignee: Kyphon SÀRL, Neuchâtel (CH)

( * ) Notice: Subject to any disclaimer, the term of this patent is extended or adjusted under 35 U.S.C. 154(b) by 242 days.

(21) Appl. No.: 10/685,139

(22) Filed: Oct. 14, 2003

(65) Prior Publication Data

US 2004/0097931 A1    May 20, 2004

Related U.S. Application Data

(60) Provisional application No. 60/422,020, filed on Oct. 29, 2002.

(51) Int. Cl.
*A61B 17/70* (2006.01)
(52) U.S. Cl. .................................................. 606/247
(58) Field of Classification Search .................. 606/61; 623/17.11–17.16
See application file for complete search history.

(56) References Cited

U.S. PATENT DOCUMENTS

| | | | |
|---|---|---|---|
| 2,456,806 A | 12/1948 | Wolfe | |
| 2,677,369 A | 5/1954 | Knowles | |
| 3,426,364 A | 2/1969 | Lumb | |
| 3,643,658 A | 2/1972 | Steinemenan | |
| 3,648,691 A | 3/1972 | Lumb | |
| 3,867,728 A | 2/1975 | Stubstad | |
| 3,875,595 A | 4/1975 | Froning | |
| 3,915,160 A * | 10/1975 | Lode et al. | 606/53 |
| 4,011,602 A | 3/1977 | Rybicki et al. | |
| 4,034,418 A | 7/1977 | Jackson | |
| 4,219,015 A | 8/1980 | Steinemann | |
| 4,257,409 A * | 3/1981 | Bacal et al. | 606/61 |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,455,690 A | 6/1984 | Homsy | |
| 4,479,491 A | 10/1984 | Martin | |
| 4,501,269 A | 2/1985 | Bagby | |

(Continued)

FOREIGN PATENT DOCUMENTS

CA          2015507         1/1991

(Continued)

OTHER PUBLICATIONS

Minns, R.J., et al., *Preliminary Design and Experimental Studies of a Novel Soft Implant for Correcting Sagittal Plane Instability in the Lumbar Spine*, Spine vol. 22, No. 16, pp. 1819-1825, © 1997, Lippincott-Raven Publishers.

(Continued)

*Primary Examiner*—Eduardo C Robert
*Assistant Examiner*—Mary Hoffman
(74) *Attorney, Agent, or Firm*—Coats and Bennett, P.L.L.C.

(57) ABSTRACT

A minimally invasive implant for the lumbosacral region of the spine. One embodiment includes an implant with a brace movably attached to a base. The brace includes a spacer and a beam. The base may be adapted to be mounted onto a S1 vertebra. The brace may be selectively positioned on the base with the spacer extending outward to contact a second vertebra.

46 Claims, 11 Drawing Sheets

U.S. PATENT DOCUMENTS

| | | | |
|---|---|---|---|
| 4,553,273 A | 11/1985 | Wu | |
| 4,554,914 A | 11/1985 | Kapp | |
| 4,573,454 A | 3/1986 | Hoffman | |
| 4,599,084 A | 7/1986 | Nashef | |
| 4,599,086 A | 7/1986 | Doty | |
| 4,604,995 A | 8/1986 | Stephens | |
| 4,611,582 A | 9/1986 | Duff | |
| 4,636,217 A | 1/1987 | Ogilvie | |
| 4,643,178 A | 2/1987 | Nastari | |
| 4,657,550 A | 4/1987 | Daher | |
| 4,685,447 A | 8/1987 | Iversen | |
| 4,686,970 A | 8/1987 | Dove et al. | |
| 4,696,290 A | 9/1987 | Steffee | |
| 4,714,469 A | 12/1987 | Kenna | |
| 4,743,256 A | 5/1988 | Brantigan | |
| 4,772,287 A | 9/1988 | Ray | |
| 4,790,303 A | 12/1988 | Steffee | |
| 4,794,918 A * | 1/1989 | Wolter | 606/69 |
| 4,827,918 A * | 5/1989 | Olerud | 606/61 |
| 4,834,757 A | 5/1989 | Brantigan | |
| 4,502,161 A | 7/1989 | Wall | |
| 4,878,915 A | 11/1989 | Brantigan | |
| 4,904,260 A | 2/1990 | Ray | |
| 4,904,261 A | 2/1990 | Dove | |
| 4,913,134 A | 4/1990 | Luque | |
| 4,923,471 A | 5/1990 | Morgan | |
| 4,932,975 A | 6/1990 | Main | |
| 4,936,848 A | 6/1990 | Bagby | |
| 4,946,378 A | 8/1990 | Hirayama | |
| 4,961,740 A | 10/1990 | Ray | |
| 4,969,888 A | 11/1990 | Scholten | |
| 5,011,484 A * | 4/1991 | Breard | 606/249 |
| 5,015,247 A | 5/1991 | Michelson | |
| 5,015,255 A | 5/1991 | Kuslich | |
| 5,026,373 A | 6/1991 | Ray | |
| 5,035,716 A | 7/1991 | Downey | |
| 5,047,055 A | 9/1991 | Bao | |
| 5,055,104 A | 10/1991 | Ray | |
| 5,059,193 A | 10/1991 | Kuslich | |
| 5,059,194 A | 10/1991 | Michelson | |
| 5,062,845 A | 11/1991 | Kuslich | |
| 5,062,850 A | 11/1991 | MacMillan | |
| 5,074,864 A * | 12/1991 | Cozad et al. | 606/54 |
| 5,084,049 A | 1/1992 | Asher et al. | |
| 5,088,869 A | 2/1992 | Greenslade | |
| 5,092,866 A | 3/1992 | Breard | |
| 5,102,412 A * | 4/1992 | Rogozinski | 606/86 A |
| 5,105,255 A | 4/1992 | Shannon | |
| 5,122,130 A | 6/1992 | Keller | |
| 5,123,926 A | 6/1992 | Pisharodi | |
| 5,127,912 A | 7/1992 | Ray | |
| 5,147,404 A | 9/1992 | Downey | |
| 5,167,662 A | 12/1992 | Hayes | |
| 5,167,665 A | 12/1992 | McKinney | |
| 5,180,381 A | 1/1993 | Aust | |
| 5,192,327 A | 3/1993 | Brantigan | |
| 5,201,734 A | 4/1993 | Cozad et al. | |
| 5,258,031 A | 11/1993 | Salib | |
| 5,263,953 A | 11/1993 | Bagby | |
| 5,275,601 A | 1/1994 | Gogolewski | |
| 5,290,312 A | 3/1994 | Kojimoto | |
| 5,300,073 A | 4/1994 | Ray | |
| 5,304,178 A | 4/1994 | Stahurski | |
| 5,306,275 A | 4/1994 | Bryan | |
| 5,306,309 A | 4/1994 | Wagner | |
| 5,352,225 A | 10/1994 | Yuan | |
| 5,360,430 A | 11/1994 | Lin | |
| 5,366,455 A | 11/1994 | Dove | |
| 5,387,213 A | 2/1995 | Breard | |
| 5,390,683 A | 2/1995 | Pisharodi | |
| 5,391,168 A * | 2/1995 | Sanders et al. | 606/253 |
| 5,395,372 A | 3/1995 | Holt | |
| 5,415,659 A * | 5/1995 | Lee et al. | 606/61 |
| 5,415,661 A | 5/1995 | Holmes | |
| 5,437,672 A | 8/1995 | Alleyne | |
| 5,443,514 A | 8/1995 | Steffee | |
| 5,454,812 A | 10/1995 | Lin | |
| 5,456,722 A | 10/1995 | McLeod | |
| 5,458,638 A | 10/1995 | Kuslich | |
| 5,458,641 A | 10/1995 | Ramirez Jimenez | |
| 5,458,643 A | 10/1995 | Oka | |
| 5,468,242 A | 11/1995 | Reisberg | |
| 5,470,333 A | 11/1995 | Ray | |
| 5,491,882 A | 2/1996 | Walston | |
| 5,496,318 A * | 3/1996 | Howland et al. | 606/249 |
| 5,505,732 A | 4/1996 | Michelson | |
| 5,507,745 A | 4/1996 | Logroscino | |
| 5,507,747 A * | 4/1996 | Yuan et al. | 606/61 |
| 5,507,823 A | 4/1996 | Walston | |
| 5,514,180 A | 5/1996 | Heggeness | |
| 5,527,312 A | 6/1996 | Ray | |
| 5,531,747 A | 7/1996 | Ray | |
| 5,534,028 A | 7/1996 | Bao | |
| 5,534,029 A | 7/1996 | Shima | |
| 5,540,689 A | 7/1996 | Sanders | |
| 5,549,679 A | 8/1996 | Kuslich | |
| 5,554,191 A | 9/1996 | Lahille | |
| 5,562,736 A | 10/1996 | Ray | |
| 5,571,191 A | 11/1996 | Fitz | |
| 5,577,995 A | 11/1996 | Walker | |
| 5,584,832 A | 12/1996 | Schlapfer | |
| 5,593,409 A | 1/1997 | Michelson | |
| 5,601,553 A | 2/1997 | Trebing | |
| 5,603,713 A | 2/1997 | Aust | |
| 5,609,634 A | 3/1997 | Voydeville | |
| 5,616,142 A | 4/1997 | Yuan | |
| 5,623,984 A | 4/1997 | Nozaki | |
| 5,628,756 A | 5/1997 | Barker, Jr. | |
| 5,645,597 A | 7/1997 | Krapiva | |
| 5,645,599 A * | 7/1997 | Samani | 623/17.16 |
| 5,653,761 A | 8/1997 | Pisharodi | |
| 5,658,286 A | 8/1997 | Sava | |
| 5,672,177 A | 9/1997 | Seldin | |
| 5,674,295 A | 10/1997 | Ray | |
| 5,674,296 A | 10/1997 | Bryan | |
| 5,676,702 A | 10/1997 | Ratron | |
| 5,690,649 A | 11/1997 | Li | |
| 5,702,392 A * | 12/1997 | Wu et al. | 606/61 |
| 5,702,452 A * | 12/1997 | Argenson et al. | 606/61 |
| 5,702,455 A | 12/1997 | Saggar | |
| 5,725,582 A | 3/1998 | Bevan | |
| 5,733,284 A * | 3/1998 | Martin | 606/248 |
| 5,741,261 A | 4/1998 | Moskovitz | |
| 5,766,251 A | 6/1998 | Koshino | |
| 5,766,252 A | 6/1998 | Henry | |
| 5,800,438 A | 9/1998 | Tuke | |
| 5,810,815 A | 9/1998 | Morales | |
| 5,824,098 A | 10/1998 | Stein | |
| 5,836,948 A | 11/1998 | Zucherman | |
| 5,860,977 A | 1/1999 | Zucherman | |
| 5,865,846 A | 2/1999 | Bryan | |
| 5,865,848 A | 2/1999 | Baker | |
| 5,876,402 A | 3/1999 | Errico | |
| 5,876,404 A | 3/1999 | Zucherman | |
| 5,879,396 A | 3/1999 | Walston | |
| 5,885,299 A | 3/1999 | Winslow | |
| 5,888,224 A | 3/1999 | Beckers | |
| 5,888,226 A | 3/1999 | Rogozinski | |
| 5,928,232 A * | 7/1999 | Howland et al. | 606/276 |
| 5,951,555 A | 9/1999 | Rehak | |
| 5,976,186 A | 11/1999 | Bao | |
| 6,001,130 A | 12/1999 | Bryan | |
| 6,022,376 A | 2/2000 | Assell | |
| 6,030,162 A | 2/2000 | Huebner | |

| | | | | | |
|---|---|---|---|---|---|
| 6,045,554 A | 4/2000 | Grooms | 6,946,000 B2 | 9/2005 | Senegas et al. |
| 6,048,204 A | 4/2000 | Klardie | 7,041,136 B2 | 5/2006 | Goble et al. |
| 6,048,342 A | 4/2000 | Zucherman | 7,048,736 B2 | 5/2006 | Robinson et al. |
| 6,048,344 A | 4/2000 | Schenk | 7,087,083 B2 | 8/2006 | Pasquet et al. |
| 6,068,630 A | 5/2000 | Zucherman | 7,163,558 B2 | 1/2007 | Senegas et al. |
| RE36,758 E | 6/2000 | Fitz | 7,201,751 B2 | 4/2007 | Zucherman et al. |
| 6,099,531 A | 8/2000 | Bonutti | 7,238,204 B2 | 7/2007 | Le Couedic et al. |
| 6,113,639 A | 9/2000 | Ray | 7,306,628 B2 | 12/2007 | Zucherman et al. |
| 6,129,730 A | 10/2000 | Bono | 7,442,208 B2 | 10/2008 | Mathieu et al. |
| 6,132,464 A * | 10/2000 | Martin .................... 623/17.15 | 7,445,637 B2 | 11/2008 | Taylor |
| 6,139,550 A | 10/2000 | Michelson | 2001/0012938 A1 | 8/2001 | Zucherman |
| 6,152,927 A | 11/2000 | Farris | 2001/0018614 A1 | 8/2001 | Bianchi |
| 6,156,067 A | 12/2000 | Bryan | 2002/0004683 A1 | 1/2002 | Michelson |
| 6,190,414 B1 | 2/2001 | Young | 2002/0016595 A1 | 2/2002 | Michelson |
| 6,193,721 B1 | 2/2001 | Michelson | 2002/0022843 A1 | 2/2002 | Michelson |
| 6,200,322 B1 | 3/2001 | Branch | 2002/0029039 A1 * | 3/2002 | Zucherman et al. .......... 606/61 |
| 6,206,922 B1 | 3/2001 | Zdeblick | 2002/0040223 A1 * | 4/2002 | Sato et al. .................... 606/61 |
| 6,217,580 B1 | 4/2001 | Levin | 2002/0065557 A1 | 5/2002 | Goble |
| 6,224,602 B1 | 5/2001 | Hayes | 2002/0072800 A1 | 6/2002 | Goble |
| 6,224,607 B1 | 5/2001 | Michelson | 2002/0077700 A1 | 6/2002 | Varga |
| 6,228,900 B1 | 5/2001 | Shen | 2002/0099376 A1 | 7/2002 | Michelson |
| 6,234,705 B1 | 5/2001 | Troxell | 2002/0116000 A1 * | 8/2002 | Zucherman et al. .......... 606/61 |
| 6,261,296 B1 | 7/2001 | Aebi | 2002/0128655 A1 | 9/2002 | Michelson |
| 6,293,949 B1 | 9/2001 | Justis | 2002/0133155 A1 | 9/2002 | Ferree |
| 6,306,136 B1 | 10/2001 | Baccelli | 2002/0143331 A1 | 10/2002 | Zucherman et al. |
| 6,352,537 B1 | 3/2002 | Strnad | 2002/0147449 A1 * | 10/2002 | Yun .......................... 606/61 |
| 6,364,883 B1 | 4/2002 | Santilli | 2002/0151895 A1 | 10/2002 | Soboleski |
| 6,368,351 B1 | 4/2002 | Glenn | 2002/0183756 A1 | 12/2002 | Michelson |
| 6,383,186 B1 | 5/2002 | Michelson | 2002/0183757 A1 | 12/2002 | Michelson |
| 6,395,030 B1 | 5/2002 | Songer | 2002/0188296 A1 | 12/2002 | Michelson |
| 6,398,783 B1 | 6/2002 | Michelson | 2003/0004572 A1 | 1/2003 | Goble |
| 6,402,750 B1 | 6/2002 | Atkinson et al. | 2003/0028250 A1 | 2/2003 | Reiley |
| 6,402,756 B1 | 6/2002 | Ralph | 2003/0040746 A1 | 2/2003 | Mitchell |
| 6,419,703 B1 | 7/2002 | Fallin | 2003/0060828 A1 | 3/2003 | Michelson |
| 6,428,542 B1 | 8/2002 | Michelson | 2003/0078668 A1 | 4/2003 | Michelson |
| 6,436,145 B1 | 8/2002 | Miller | 2003/0109882 A1 * | 6/2003 | Shirado et al. ............... 606/61 |
| 6,440,169 B1 | 8/2002 | Elberg et al. | 2003/0153915 A1 | 8/2003 | Nekozuka et al. |
| 6,451,019 B1 * | 9/2002 | Zucherman et al. ........ 606/249 | 2003/0181912 A1 | 9/2003 | Michelson |
| 6,454,771 B1 | 9/2002 | Michelson | 2003/0191471 A1 | 10/2003 | Michelson |
| 6,458,131 B1 | 10/2002 | Ray | 2003/0191472 A1 | 10/2003 | Michelson |
| 6,527,776 B1 | 3/2003 | Michelson | 2003/0191532 A1 | 10/2003 | Goble |
| 6,558,423 B1 | 5/2003 | Michelson | 2003/0204259 A1 | 10/2003 | Goble |
| 6,558,686 B1 | 5/2003 | Darouiche | 2003/0204261 A1 | 10/2003 | Eisermann et al. |
| 6,565,570 B2 | 5/2003 | Sterett | 2004/0006391 A1 | 1/2004 | Reiley |
| 6,565,605 B2 * | 5/2003 | Goble et al. ............. 623/17.11 | 2004/0049272 A1 | 3/2004 | Reiley |
| 6,579,318 B2 | 6/2003 | Varga | 2004/0049273 A1 | 3/2004 | Reiley |
| 6,579,319 B2 | 6/2003 | Goble | 2004/0049274 A1 | 3/2004 | Reiley |
| 6,582,433 B2 | 6/2003 | Yun | 2004/0049275 A1 | 3/2004 | Reiley |
| 6,582,437 B2 | 6/2003 | Dorchak | 2004/0049276 A1 | 3/2004 | Reiley |
| 6,589,243 B1 * | 7/2003 | Viart et al. ................... 606/61 | 2004/0049277 A1 | 3/2004 | Reiley |
| 6,592,586 B1 | 7/2003 | Michelson | 2004/0049278 A1 | 3/2004 | Reiley |
| 6,610,091 B1 | 8/2003 | Reiley | 2004/0049281 A1 | 3/2004 | Reiley |
| 6,620,163 B1 | 9/2003 | Michelson | 2004/0087948 A1 | 5/2004 | Suddaby |
| 6,626,944 B1 | 9/2003 | Taylor | 2004/0097931 A1 | 5/2004 | Mitchell |
| 6,641,614 B1 | 11/2003 | Wagner et al. | 2004/0111154 A1 | 6/2004 | Reiley |
| 6,645,207 B2 | 11/2003 | Dixon et al. | 2004/0116927 A1 | 6/2004 | Graf |
| 6,652,527 B2 * | 11/2003 | Zucherman et al. ........... 606/61 | 2004/0117022 A1 | 6/2004 | Marnay et al. |
| 6,669,729 B2 | 12/2003 | Chin | 2004/0122427 A1 | 6/2004 | Holmes |
| 6,695,842 B2 | 2/2004 | Zucherman et al. | 2004/0127989 A1 | 7/2004 | Dooris |
| 6,699,246 B2 | 3/2004 | Zucherman et al. | 2004/0143268 A1 | 7/2004 | Falahee |
| 6,709,435 B2 | 3/2004 | Lin | 2004/0143332 A1 | 7/2004 | Krueger et al. |
| 6,712,852 B1 | 3/2004 | Chung | 2004/0153157 A1 | 8/2004 | Keller |
| 6,723,126 B1 | 4/2004 | Berry | 2004/0181226 A1 | 9/2004 | Michelson |
| 6,730,127 B2 | 5/2004 | Michelson | 2004/0181229 A1 | 9/2004 | Michelson |
| 6,733,534 B2 | 5/2004 | Sherman | 2004/0186475 A1 | 9/2004 | Falahee |
| 6,752,831 B2 | 6/2004 | Sybert | 2004/0186476 A1 | 9/2004 | Michelson |
| 6,755,841 B2 | 6/2004 | Fraser | 2004/0210313 A1 | 10/2004 | Michelson |
| 6,761,720 B1 | 7/2004 | Senegas | 2004/0210314 A1 | 10/2004 | Michelson |
| 6,783,527 B2 | 8/2004 | Drewry | 2004/0220678 A1 | 11/2004 | Chow |
| 6,800,670 B2 | 10/2004 | Shen | 2004/0225363 A1 | 11/2004 | Richelsoph |
| 6,811,567 B2 | 11/2004 | Reiley | 2004/0230201 A1 | 11/2004 | Yuan |
| 6,835,205 B2 | 12/2004 | Atkinson et al. | 2004/0230304 A1 | 11/2004 | Yuan |
| 6,936,071 B1 | 8/2005 | Marnay et al. | 2004/0230307 A1 | 11/2004 | Eisermann |

| | | | | | | |
|---|---|---|---|---|---|---|
| 2004/0236334 | A1 | 11/2004 | Michelson | FR | 2717675 A1 | 9/1995 |
| 2004/0236335 | A1 | 11/2004 | Michelson | FR | 2722087 A1 | 1/1996 |
| 2004/0243240 | A1 | 12/2004 | Beaurain et al. | FR | 2722088 | 1/1996 |
| 2005/0010293 | A1 | 1/2005 | Zucherman et al. | FR | 2722088 A1 | 1/1996 |
| 2005/0021145 | A1 | 1/2005 | De Villiers et al. | FR | 2722980 A1 | 2/1996 |
| 2005/0027297 | A1 | 2/2005 | Michelson | FR | 2724554 | 3/1996 |
| 2005/0027298 | A1 | 2/2005 | Michelson | FR | 2724554 A1 | 3/1996 |
| 2005/0043802 | A1 | 2/2005 | Eisermann et al. | FR | 2725892 A1 | 4/1996 |
| 2005/0049708 | A1 | 3/2005 | Atkinson et al. | FR | 2730156 A1 | 8/1996 |
| 2005/0065611 | A1 | 3/2005 | Huppert et al. | FR | 2775183 A1 | 8/1999 |
| 2005/0102029 | A1 | 5/2005 | Blain | FR | 2780269 A1 | 12/1999 |
| 2005/0113842 | A1 | 5/2005 | Bertagnoli et al. | FR | 2782911 A1 | 3/2000 |
| 2005/0159818 | A1 | 7/2005 | Blain | FR | 2806614 A1 | 9/2001 |
| 2005/0159819 | A1 | 7/2005 | McCormack et al. | FR | 2806616 A1 | 9/2001 |
| 2005/0165398 | A1 | 7/2005 | Reiley | FR | 2816197 A1 | 5/2002 |
| 2005/0203652 | A1 | 9/2005 | Hawkins et al. | GB | 780652 | 8/1957 |
| 2005/0203624 | A1 | 9/2005 | Serhan et al. | JP | 02-224660 | 9/1990 |
| 2005/0228391 | A1 | 10/2005 | Levy et al. | JP | 09-075381 | 3/1997 |
| 2005/0261768 | A1 | 11/2005 | Trieu | JP | 10-179622 | 7/1998 |
| 2005/0288672 | A1 | 12/2005 | Ferree | SU | 988281 | 1/1983 |
| 2006/0004447 | A1 | 1/2006 | Mastrorio et al. | SU | 1484348 A1 | 6/1989 |
| 2006/0015181 | A1 | 1/2006 | Elberg | WO | WO 90/00037 | 1/1990 |
| 2006/0036326 | A1 | 2/2006 | Baumgartner et al. | WO | WO 91/16018 | 10/1991 |
| 2006/0064165 | A1 | 3/2006 | Zucherman et al. | WO | WO 94/21185 | 9/1994 |
| 2006/0084983 | A1 | 4/2006 | Kim | WO | WO 94/26192 | 11/1994 |
| 2006/0084985 | A1 | 4/2006 | Kim | WO | WO 94/26193 | 11/1994 |
| 2006/0084987 | A1 | 4/2006 | Kim | WO | WO 94/26195 | 11/1994 |
| 2006/0084988 | A1 | 4/2006 | Kim | WO | WO 95/35067 | 12/1995 |
| 2006/0085069 | A1 | 4/2006 | Kim | WO | WO 96/08206 A1 | 3/1996 |
| 2006/0089654 | A1 | 4/2006 | Lins et al. | WO | WO 96/39975 | 12/1996 |
| 2006/0089719 | A1 | 4/2006 | Trieu | WO | WO 98/20939 | 5/1998 |
| 2006/0106381 | A1 | 5/2006 | Ferree et al. | WO | WO 98/48717 | 11/1998 |
| 2006/0106397 | A1 | 5/2006 | Lins | WO | WO 98/55038 | 12/1998 |
| 2006/0111728 | A1 | 5/2006 | Abdou | WO | WO 99/26562 | 6/1999 |
| 2006/0122620 | A1 | 6/2006 | Kim | WO | WO 99/40866 | 8/1999 |
| 2006/0136060 | A1 | 6/2006 | Taylor | WO | WO 99/42051 | 8/1999 |
| 2006/0184247 | A1 | 8/2006 | Edidin et al. | WO | WO 99/56653 | 11/1999 |
| 2006/0184248 | A1 | 8/2006 | Edidin et al. | WO | WO 99/59669 | 11/1999 |
| 2006/0195102 | A1 | 8/2006 | Malandain | WO | WO 00/04851 | 2/2000 |
| 2006/0217726 | A1 | 9/2006 | Maxy et al. | WO | WO 00/13619 | 3/2000 |
| 2006/0264938 | A1 | 11/2006 | Zucherman et al. | WO | WO 00/13620 | 3/2000 |
| 2006/0271044 | A1 | 11/2006 | Petrini et al. | WO | WO 00/38582 | 7/2000 |
| 2006/0293662 | A1 | 12/2006 | Boyer, II et al. | WO | WO 00/53126 | 9/2000 |
| | | | | WO | WO 01/26566 A1 | 4/2001 |
| | | FOREIGN PATENT DOCUMENTS | | WO | WO 01/28442 A1 | 4/2001 |
| DE | | 2821678 A1 | 11/1979 | WO | WO 02/34120 A2 | 5/2002 |
| DE | | 2821678 A1 | 4/1980 | WO | WO 02/085226 A1 | 10/2002 |
| DE | | 3113142 A1 | 1/1982 | WO | WO 03/057055 A1 | 7/2003 |
| DE | | 4012622 C1 | 7/1991 | WO | WO 03/101350 A1 | 12/2003 |
| DE | | 4409833 | 10/1995 | WO | WO 2004/047691 A1 | 6/2004 |
| DE | | 4414781 | 11/1995 | WO | WO 2004/071358 A1 | 8/2004 |
| DE | | 201 12 123 U1 | 9/2001 | WO | WO 2004/098465 A1 | 11/2004 |
| DE | | 101 35 771 A1 | 2/2003 | WO | WO 2005/009300 A1 | 2/2005 |
| EP | | 140790 A2 | 10/1984 | WO | WO 2005/044118 A1 | 5/2005 |
| EP | | 146347 A1 | 12/1984 | WO | WO 2005/110258 A1 | 11/2005 |
| EP | | 322334 A1 | 12/1988 | WO | WO 2007/034516 A1 | 3/2007 |
| EP | | 0322334 B1 | 2/1992 | | | |
| EP | | 0307241 B1 | 12/1992 | | OTHER PUBLICATIONS | |
| EP | | 0677277 A2 | 10/1995 | | | |
| EP | | 0767636 B1 | 4/1997 | | | |
| EP | | 1138268 A1 | 10/2001 | | | |
| FR | | 2623085 | 5/1989 | | | |
| FR | | 2623085 A1 | 5/1989 | | | |
| FR | | 2625097 A1 | 6/1989 | | | |
| FR | | 2681525 A1 | 3/1993 | | | |
| FR | | 2700941 A1 | 8/1994 | | | |
| FR | | 2703239 A1 | 10/1994 | | | |
| FR | | 2705227 | 11/1994 | | | |
| FR | | 2707864 A1 | 1/1995 | | | |
| FR | | 2717066 | 9/1995 | | | |
| FR | | 2717068 | 9/1995 | | | |
| FR | | 2717675 | 9/1995 | | | |

Waldemar Link, brochure entitled *Wirbelsäulen-Chirurgie: Instrumentarium Und Implantate Zur Wirbelsäulen-Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77-86, © 1990 Raven Press, Ltd., New York.

Richard W. Porter, MD, FRCS, FRCSE, *Spinal Stenosis and Neurogenic Claudication*, Spine vol. 21, No. 17, pp. 2046-2052, © 1996, Lippincott-Raven Publishers.

Supplementary European Search Report dated Aug. 31, 2004.
International Search Report dated Nov. 5, 2004.
International Search Report dated Nov. 15, 2004.
International Search Report dated Nov. 18, 2004.

International Search Report dated Jan. 25, 2005.
International Search Report for PCT/US06/10521 (Mailed Nov. 22, 2006).
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," Spine, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," Spine, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," Spine, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.
Petrini et al., "Stabilizzazione Elastica," Patologia Degenerative del Rachide Lombare, Oct. 5-6, 2001, Rimini.
Porter, "Spinal Stenosis and Neurogenic Claudication," Spine, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," Spine, 2005, pp. 744-749, vol. 30, No. 7.
Scarfò, "Instability/Stenosis: Holistic Approach for Less Invasive Surgery," date unknown, University of Siena, Siena, Italy.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," Spine, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.
Senegas et al., "Stabilisation Lombaire Souple," Instabilité Vértebrates Lombaires, Gastambide, ed., 1995, pp. 122-132, Expansion Scientifique Française, Paris, France.
Senegas, "La Ligamentoplastie Inter Vertébrale Lombaire, Alternative a L'Arthrodèse," La Revue de Medécine Orthopedique, Jun. 1990, pp. 33-35, No. 20.
Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.
Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.
Senegas, "Rencontre," Maîtrise Orthopédique, May 1995, pp. 1-3, No. 44.
Serhan, "Spinal Implants: Past, Present, and Future," 19th International IEEE/EMBS Conference, Oct. 30-Nov. 2, 1997, pp. 2636-2639, Chicago, Illinois.
Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.
Sulzer Innotec, "DIAM—Modified CAD Geometry and Meshing," date unknown.
Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.
Taylor et al., "Surgical Requirement for the Posterior Control of the Rotational Centers," date unknown.
Taylor et al., "Technical and Anatomical Considerations for the Placement of a Posterior Interspinous Stabilizer," 2004, pp. 1-10, Medtronic Sofamor Danek USA, Inc., Memphis, Tennessee.
Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Wittenberg et al., "Flexibility and Distraction after Monosegmental and Bisegmental Lumbrosacral Fixation with Angular Stable Fixators," Spine, 1995, pp. 1227-1232, vol. 20, No. 11.

Zucherman et al., "Clinical Efficacy of Spinal Instrumentation in Lumbar Degenerative Disc Disease," Spine, Jul. 1992, pp. 834-837, vol. 17, No. 7.

* cited by examiner

INTERSPINOUS PROCESS AND SACRUM IMPLANT AND METHOD

CLAIM OF PRIORITY

This application claims priority to U.S. Provisional Application No. 60/422,020, filed on Oct. 29, 2002, entitled "INTERSPINOUS PROCESS AND SACRUM IMPLANT AND METHOD", which is incorporated herein by reference.

CROSS REFERENCE TO RELATED APPLICATIONS

This application is related to U.S. Provisional Application No. 60/421,915, filed Oct. 29, 2002, entitled "INTERSPINOUS PROCESS IMPLANT WITH RADIOLUCENT SPACER AND LEAD-IN TISSUE EXPANDER", which are incorporated herein by reference. This application is also related to U.S. patent application Ser. No. 10/230,505, filed Aug. 29, 2002, entitled "DEFLECTABLE SPACER FOR USE AS AN INTERSPINOUS PROCESS IMPLANT AND METHOD", which is incorporated herein by reference.

FIELD OF THE INVENTION

This invention relates to an implant that is adapted to be placed between the L5 and the S1 vertebrae and method.

BACKGROUND OF THE INVENTION

As the present society ages, it is anticipated that there will be an increase in degenerative and dysfunctional spinal conditions including degenerative disk and joint diseases, spinal fractions and other problems. Pain associated with such conditions can be relieved by medication and/or surgery. The lumbosacral junction itself is exposed to significant axial, translational and rotational loads that can exacerbate the pain experienced from these degenerative conditions. Effectively managing lumbosacral region instability and pain can require that sagittal balance and neurological function be maintained. This is traditionally done by internal fixation and/or bone fusion.

Over the years, a variety of implants have been developed in order to relieve the pain associated with such degenerative and dysfunctional conditions. For example, U.S. Pat. Nos. 5,127,912, 5,300,073 and 6,197,028 to Ray et al. are related patents that disclose a sacral implant system.

U.S. Pat. No. 4,773,402 to Asher et al. is directed to a dorsal trans-sacral surgical implant.

U.S. Pat. No. 4,047,523 to Hall discloses a surgical sacral anchor implant that is a surgical implant for securing a cable to the sacrum to correct the curvature of the spine.

None of these solutions provide an implant that is minimally invasive while restoring stability to the region without interfering with natural movement. Nor are the implants easily adjustable after the surgery has been completed. Accordingly, what is needed is an implant for restoring stability to the lower back.

SUMMARY OF THE INVENTION

Embodiments of the present invention are directed to providing a minimally invasive implant for alleviating discomfort and lack of stability in the lumbosacral region of the spine. The implant includes a base for attaching to the medial sacral lamina. A spacer is provided that engages the base and is positioned to abut the spinous process of the L5 vertebrae.

Other aspects, objects, features, and elements of the embodiments of the invention are described or are evident from the accompanying specification, claims and figures.

DETAILED DESCRIPTION OF THE PREFERRED EMBODIMENTS OF THE INVENTION

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents, patent publications, and patent applications cited in this application are incorporated herein by reference.

Figure 1:
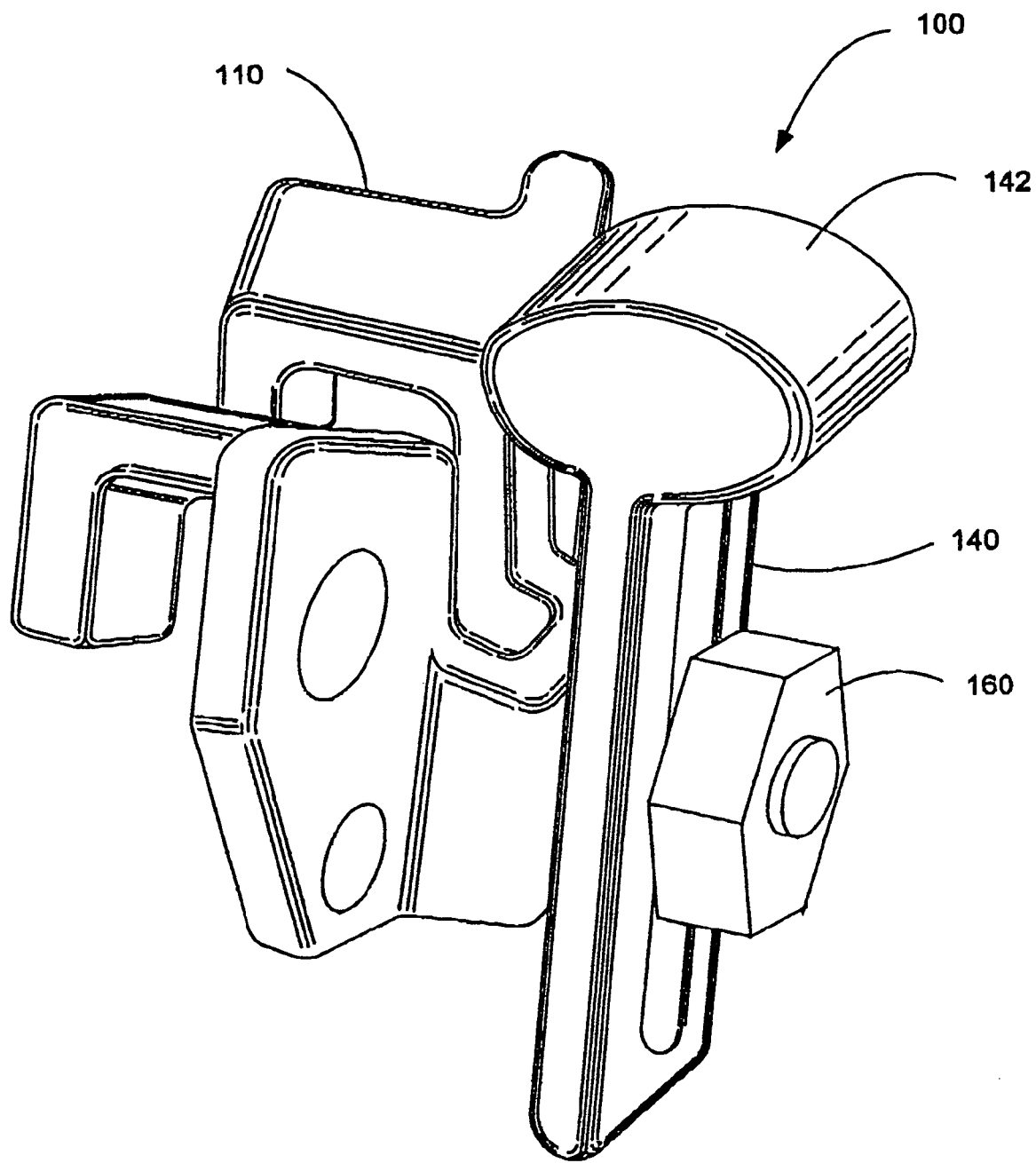
FIG. 1 is a side perspective view of an embodiment of the assembled implant of the invention.

Turning now to FIG. 1, a side perspective view of an embodiment of the assembled implant 100 of the invention. A base 110 is provided that engages the median sacral lamina upon implantation. A beam 140 and spacer 142 are attached to the base 110 and a nut 160 or other suitable device holds the beam 140 to the base 110. The beam 140 can be adjusted vertically to enable the spacer 142 to engage the spinous process of the L5 vertebra to achieve a desired amount of spacing between the L5 and S1 vertebra and to spread the mechanical load from the L5 spinous process across the implant. As desired, implant 100 can be made of titanium which is radiopague. Other suitable material includes by way of example only polyetheretherketone (PEEK), polyetherketoneketone (PEKK), polyetherketone (PEK), polyetherketoneetherketoneketone (PEKEKK), and polyetheretherketoneketone (PEEKK), all of which are radiolucent.

Figure 2A:
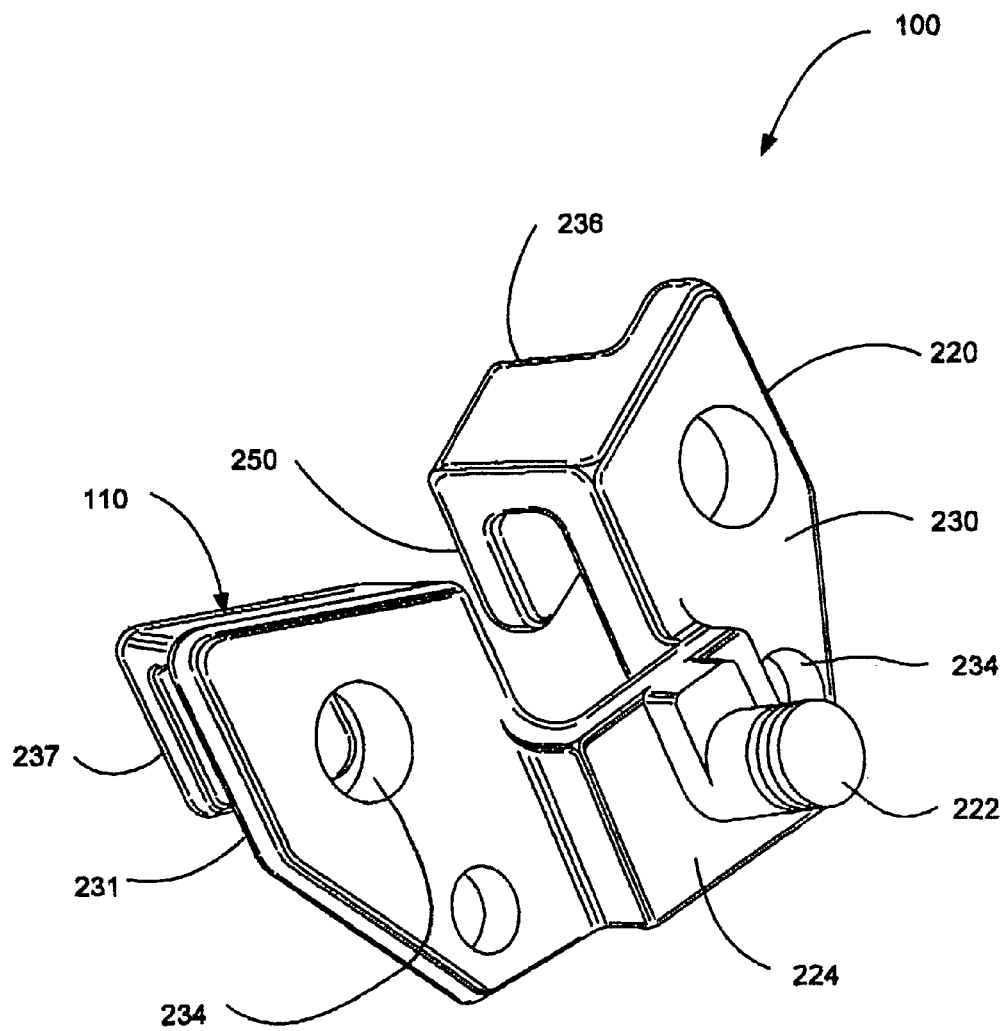
FIG. 2A is a perspective side view of an embodiment of the base of the implant of the invention.

The base 110 is shown in a perspective view in FIG. 2A. The base 110 has a body 220 with a threaded post 222 extending from a central platform 224 thereof. The central platform can be raised as shown to enable the base 110 to engage the median sacral lamina without interfering with the anatomy thereof. The post 222 is of a length to fit within the elongated aperture of the beam 140 and engage a nut 160 on the other side thereof. The nut 160 can be tightened to hold the beam in place. As will be appreciated by those of skill in the art, where another mechanism is employed to secure the beam 140 onto the post 222, threading may not be required. Alternatively, a hexagonal recess 222 (FIG. 2B) can be provided to enable the nut 160 to be tightened by an Allen wrench. Alternatively, the nut 160 can have a hexagonal outer shape to facilitate tightening thereof.

Figure 2B:
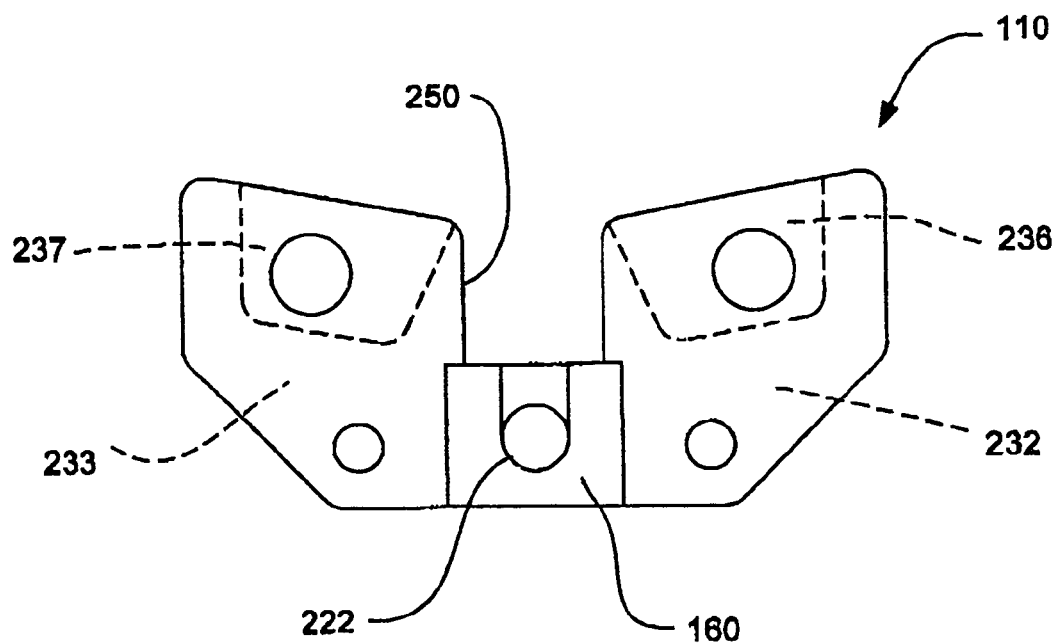
FIG. 2B is a cross-sectional plan view of an embodiment of the base of the implant of the invention.
Figure 2C:
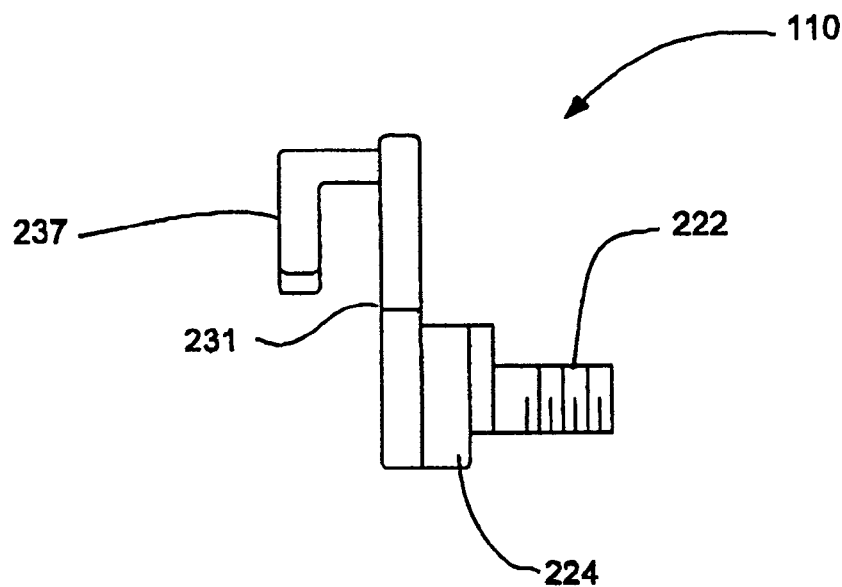
FIG. 2C is a left side view of the embodiment of Figure FIG. 2A.

The central platform 224 of the body 220 extends to a first portion or flange 230 and a second portion or flange 231, on either side of the platform 224. Each of the portions 230, 231 can also be provided with one or more apertures 234 for engaging, for example, screws 239 to further secure the base 110 to the sacrum (shown in more detail with respect to FIG. 5B described below). The portions 230, 231 are configured such that one surface 232, 233 (FIG. 2B) of each portion abuts the sacrum. At least one of the portions 230, 231 extends into a hook 236 for engaging the median sacral lamina. Preferably, each of the portions 230, 231 extends into a corresponding hook 236, 237 for engaging a first and second portion of the medial sacral lamina. FIG. 2B shows a posterior view of an embodiment of the base 110 of the implant of the invention. As evidenced from this view, the flanges 230, 231 are angled away from each other to facilitate the hooks 236, 237 engaging the median sacral lamina. The gap 250 between the flanges 230, 231 enable the base 110 to engage the sacrum. FIG. 2C shows a side view of the base 110 with the side 231 of the base 110, the hook 237, the platform 224 and the threaded post 222.

Figure 3A:
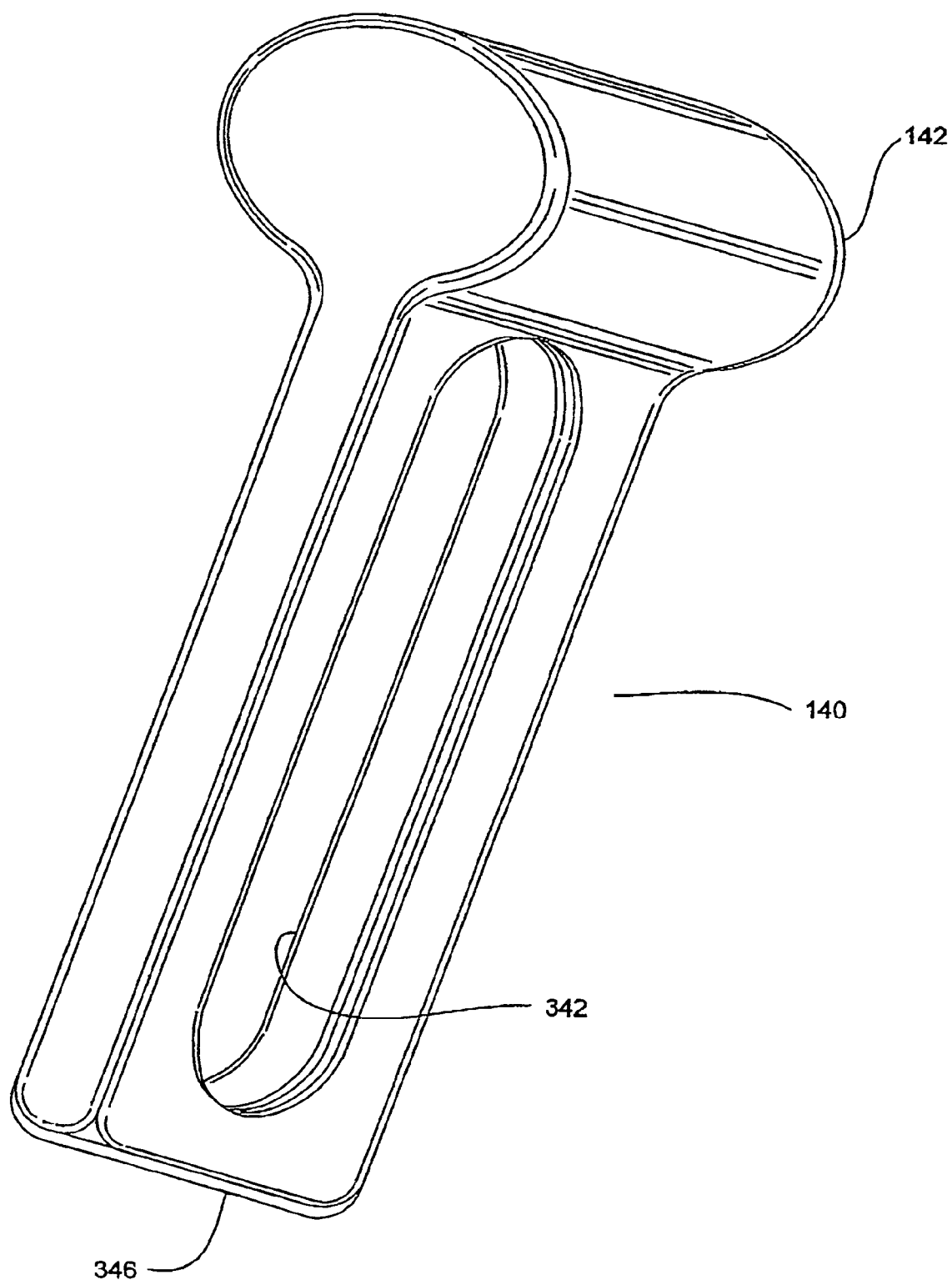
FIG. 3A is a perspective view of an embodiment of the beam and spacer of the implant of the invention.
Figure 3B:
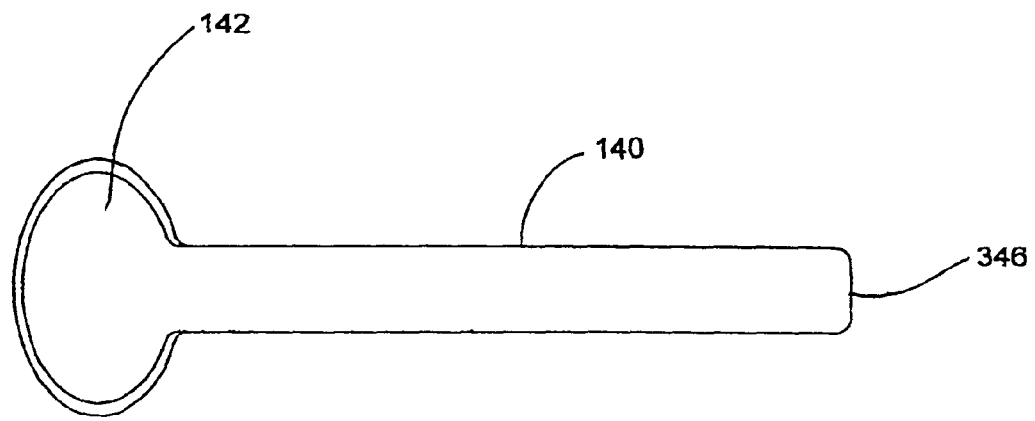
FIG. 3B is side view of an embodiment of the beam and spacer of the implant of the invention.
Figure 3C:
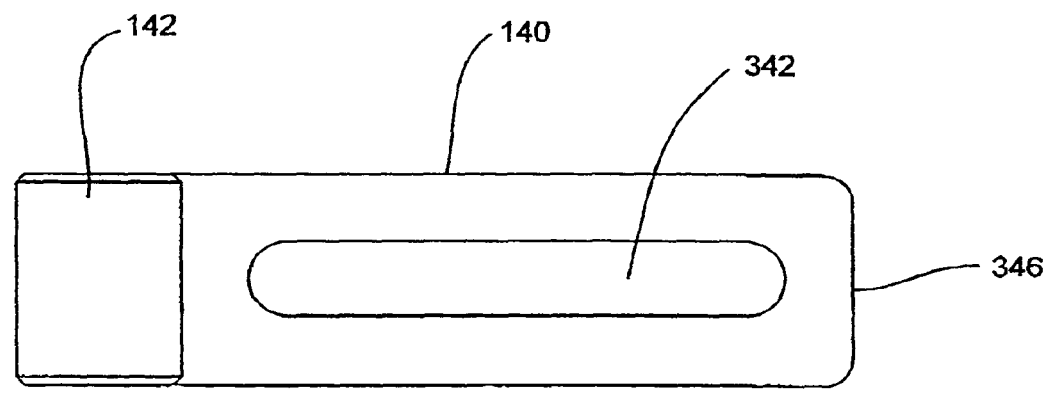
FIG. 3C is a plan view of an embodiment of the beam and spacer of the implant of the invention.

FIG. 3A is a perspective view of the beam 140 where the spacer 142, at one end thereof separated from the distal end 346, is depicted. The beam 140 has an elongated aperture 342 along a portion of its length. The elongated aperture 342 has a width sufficient to enable the post 222 of the base 110 to pass therethrough, but not so wide that when the fixation mechanism, such as the nut 160, is attached to the post 222, that the fixation mechanism would not secure the beam 140 to the base 110 at a desired location of the beam 140 relative to the base 110. Rather, the width is such that the post 222 passes through the aperture 342, and is engaged by the nut 160, or other fixation mechanism, to hold the beam 140 to the base 110.

Figure 3D:
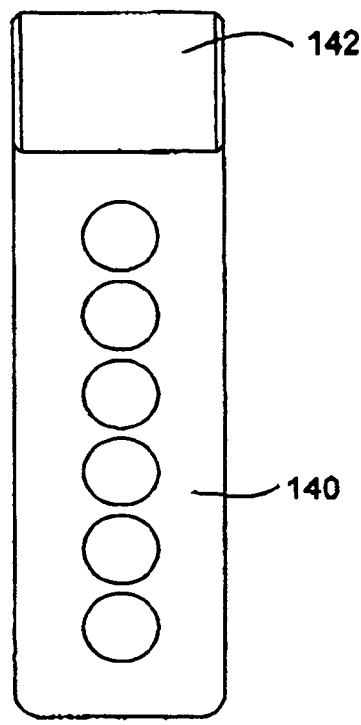
FIGS. 3D through 3G are plan views of alternative embodiments of the beam and spacer of the implant of the invention shown in FIG. 3A.
Figure 3E:
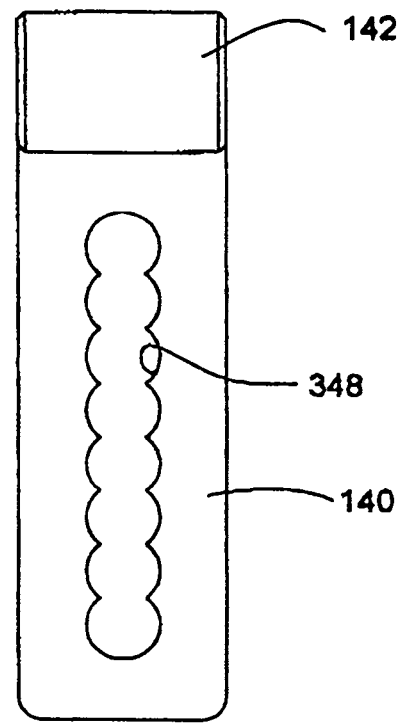
Figure 3F:
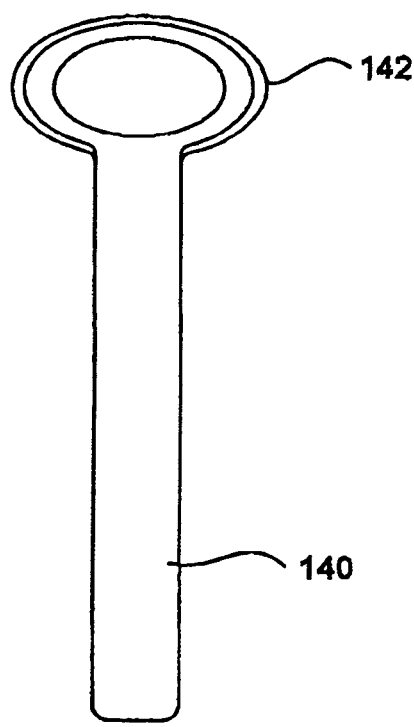
Figure 3G:
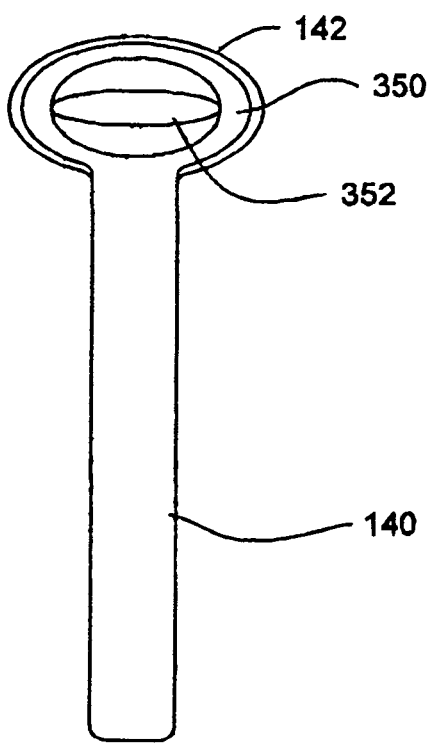

The spacer 142 is shaped so that it has a bulbous profile, as shown in FIG. 3A. In this embodiment, the spacer 142 is elliptically shaped. However, the spacer 142 can also be oval, ovoid, egg, cylindrical and racetrack (FIG. 3F) in shape. The spacer can also be hollow (FIG. 3F) to make the spacer more flexible and deflectable. Further, the spacer can be made in multiple pieces with an outer spacer spaced 350 from an inner spacer 352 (FIG. 3G) to allow for deflection of the spacer due to backward bending of the patient. This beam 140 includes the previously described elongated slot 342 which allows the spacer 140 to be positioned in a variety of positions relative to the base 110 in order for the implant 100 to adjust to the structure and shape of the spine of the patient. Additionally, the aperture 342 can be replaced by a plurality of apertures along its length as shown in FIG. 3D, any one of which can be sized to accept the post 222 of the base 110. Alternatively, the aperture 342 can have an interior surface that is scalloped 348, as shown in FIG. 3E. In such a configuration, each scallop 348 is dimensioned to accept the post 222. All these embodiments assist in the placement of the beam 140 relative to the base 110.

Figure 4A:
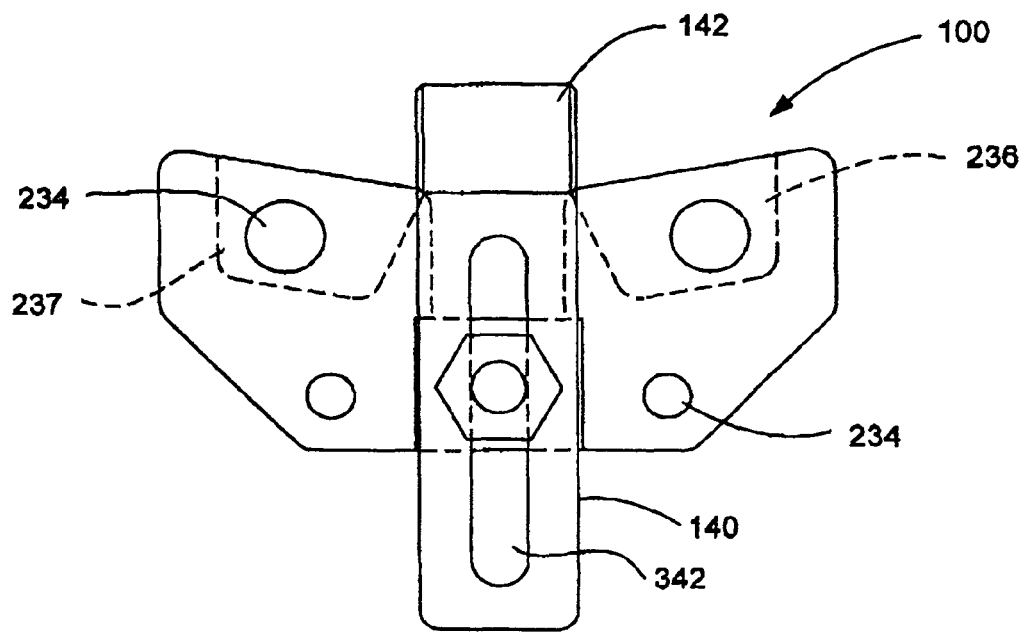
FIG. 4A is a posterior view of an embodiment of the assembled implant of the invention.
Figure 4B:
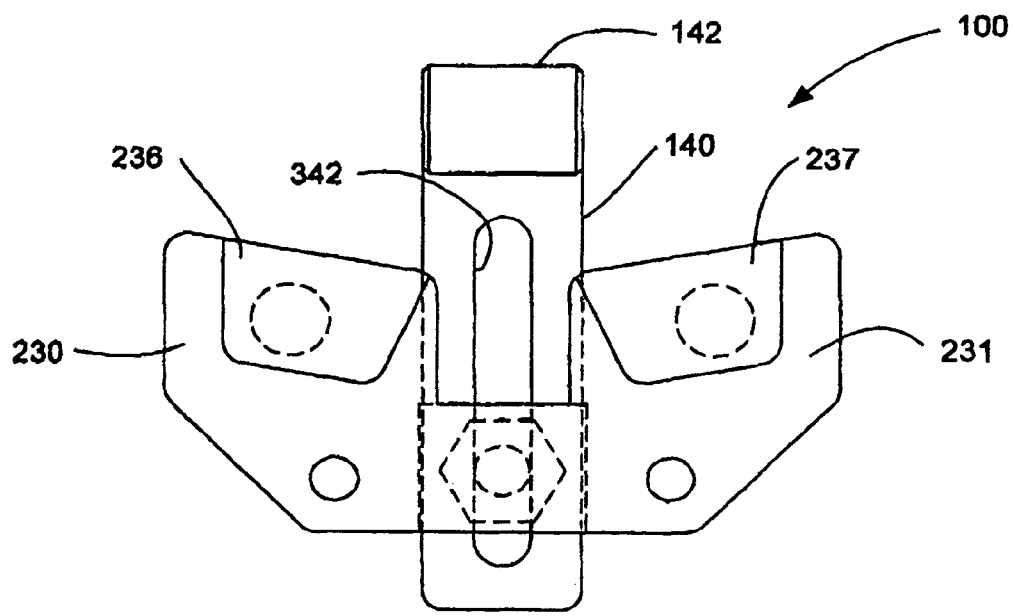
FIG. 4B is an anterior view of an embodiment of the assembled implant of the invention.

FIG. 4A shows a posterior view of an embodiment of the implant 100 in its assembled condition, while FIG. 4B shows an anterior view of the implant 100 in its assembled condition. As evidenced by the figures, the beam 140 can be positioned relative to the base 110 so that the spacer 142 sits substantially above the base 110, as shown in FIG. 4A, or so that the spacer 142 sits flush with the tops of the flanges 230, 231.

Figure 4C:
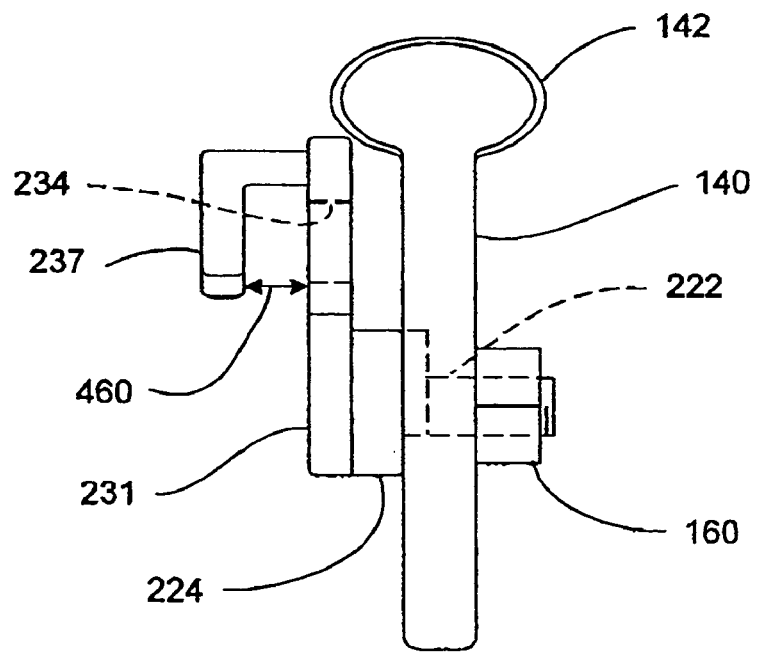
FIG. 4C is a side view of an embodiment of the assembled implant of the invention.

FIG. 4C shows a side view of an embodiment of the implant 100 assembled. As evidenced by FIG. 4C, the hooks 236, 237 are configured to provide a space 460 between the flange 230, 231 and the hook 236, 237 into which the median sacral lamina fits.

Figure 4D:
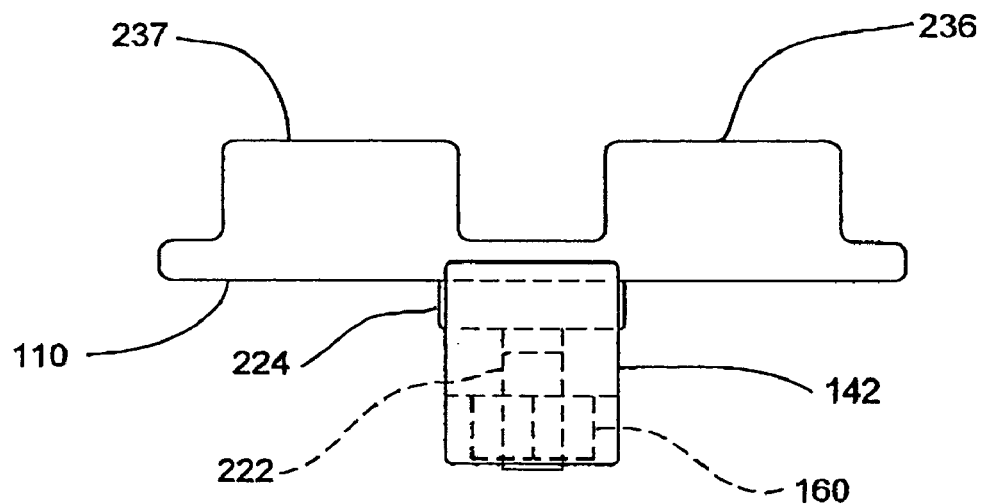
FIG. 4D is a top view of an embodiment of the assembled implant of the invention.

FIG. 4D shows a top view of the assembled implant 100 of an embodiment of the invention with the upper surface of the flanges 236, 237, the upper surface of the central platform 224 of the body, and the nut 160 engaging the post 222 of the base 110.

As will be appreciated by those of skill in the art, the implant 100 of the invention can be manufactured from a variety of biocompatible materials including titanium, suitable medical grade alloys such as nitinol, or thermoplastics using a variety of techniques such as extrusion, injection, and compression molding and/or machining techniques. Additionally, the implant 100 can have a structural frame that is comprised of a second material. For example, a structural frame of titanium can be provided which is surrounded by an appropriate thermoplastic to achieve the desired final shape of the implant in accordance with the teachings of the invention.

For example, at least part of the implant can be comprised of a polymer. The polymer can be, for example, a polyketone such as polyetheretherketone (PEEK), as previously indicated. Still, more specifically, the material can be PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com). The implant 100 can be formed by extrusion, injection, compression molding and/or machining techniques with such material. This material has appropriate physical and mechanical properties and is suitable for carrying and spreading the physical load. Further, in this embodiment the PEEK has the following approximate properties:

| Density | 1.3 g/cc |
| --- | --- |
| Rockwell M | 99 |
| Rockwell R | 126 |
| Tensile Strength | 97 MPa |
| Modulus of Elasticity | 3.5 GPa |
| Flexural Modulus | 4.1 Gpa |

It should be noted that the material selected could also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

As will be appreciated by those of skill in the art, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention. The spacer can also be comprised of polyetherketoneketone (PEKK).

Other materials that can be used include polyetherketone (PEK), polyetherketoneetherketoneketone (PEKEKK), and polyetheretherketoneketone (PEEKK), and, generally, a polyaryletheretherketone. Further, other polyketones can be used as well as other thermoplastics. The spacer can also be made of titanium.

Reference to appropriate polymers that can be used in the spacer can be made to the following documents. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and PCT Publication WO 02/00270 A1, dated Jan. 3, 2002, entitled "Bio-Compatible Polymeric Materials."

Other materials such as Bionate®, polycarbonate urethane, available from the Polymer Technology Group, Berkeley, Calif. (www.polymertech.com), may also be appropriate because of the good oxidative stability, biocompatibility, mechanical strength and abrasion resistance. Other thermoplastic materials and other high molecular weight polymers can be used as well without departing from the scope of the invention.

Figure 5A:
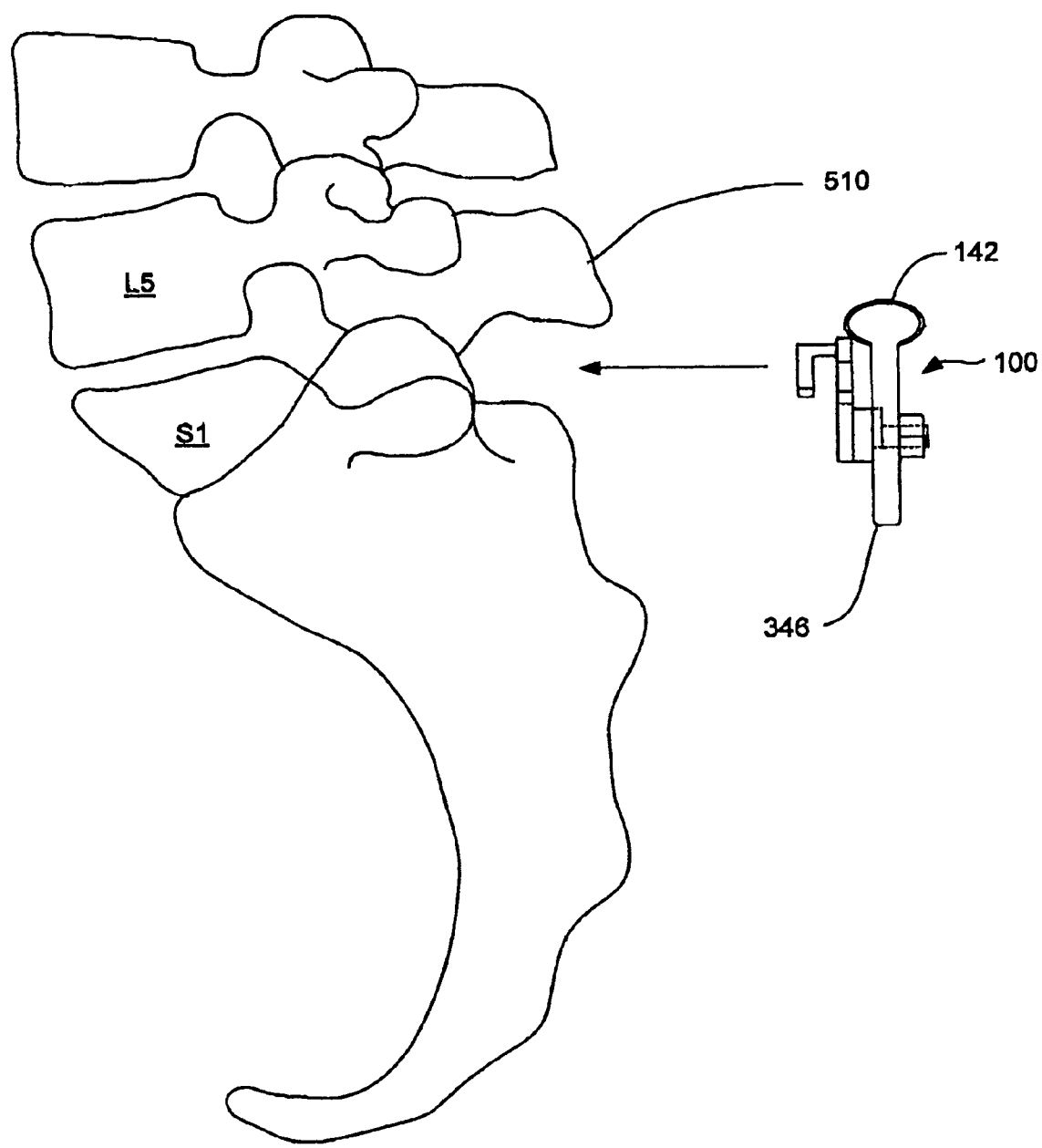
FIG. 5A is a side view of an embodiment of the implant of the invention implanted between the S1 and L5 vertebrae in the spine.

FIG. 5A shows a side view of an embodiment of the implant 100 of the invention implanted between the S1 and the L5 vertebrae. As evidenced in this figure, the spacer 142 is positioned so that it abuts the spinous process 510 of the L5 vertebrae. The width of the spacer 142 is such that it enables the spacer 142 to engage the spinous process of the L5 vertebrae while enabling the mechanical load of the L5 vertebrae to be spread out over the spacer 142.

Figure 5B:
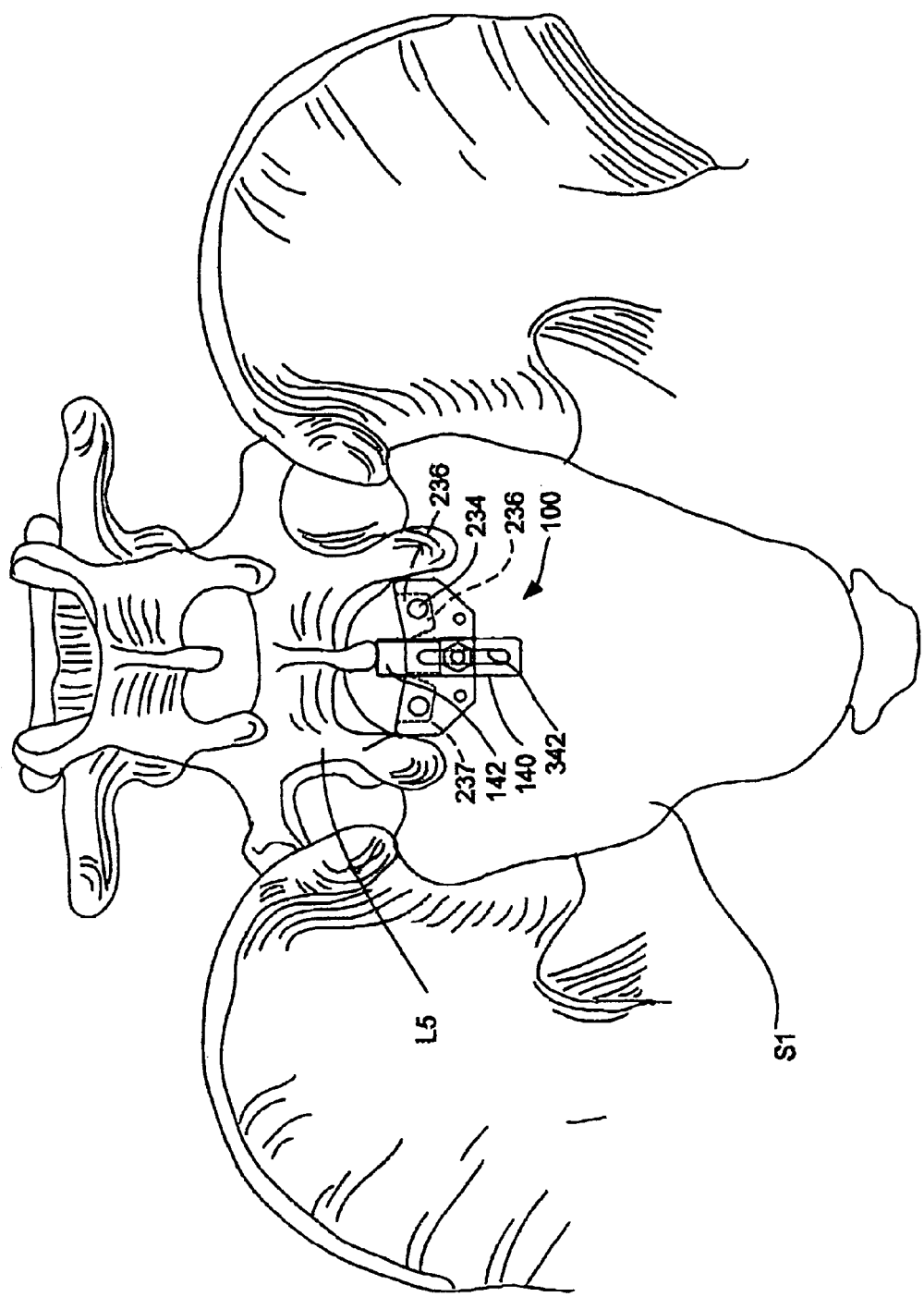
FIG. 5B is a posterior view of an embodiment of the implant of the invention implanted between the S1 and L5 vertebrae in the spine.

FIG. 5B illustrates a posterior view of an embodiment of the implant 100 of the invention implanted between the S1 and the L5 vertebrae. This perspective also shows the spacer 142 positioned to abut the spinous process of the L5 vertebrae. However, as is more readily apparent from this view, the positioning of the spacer 142 relative to the spinous process is facilitated by adjusting the position of the spacer 142 by moving the beam 140 relative to the post 222 in a first or second direction along the elongated aperture 342. Additionally, as will be apparent to those of skill in the art, the positioning of the spacer 142 relative to the spinous process can also be adjusted at a later time (e.g., after implant).

Figure 6:
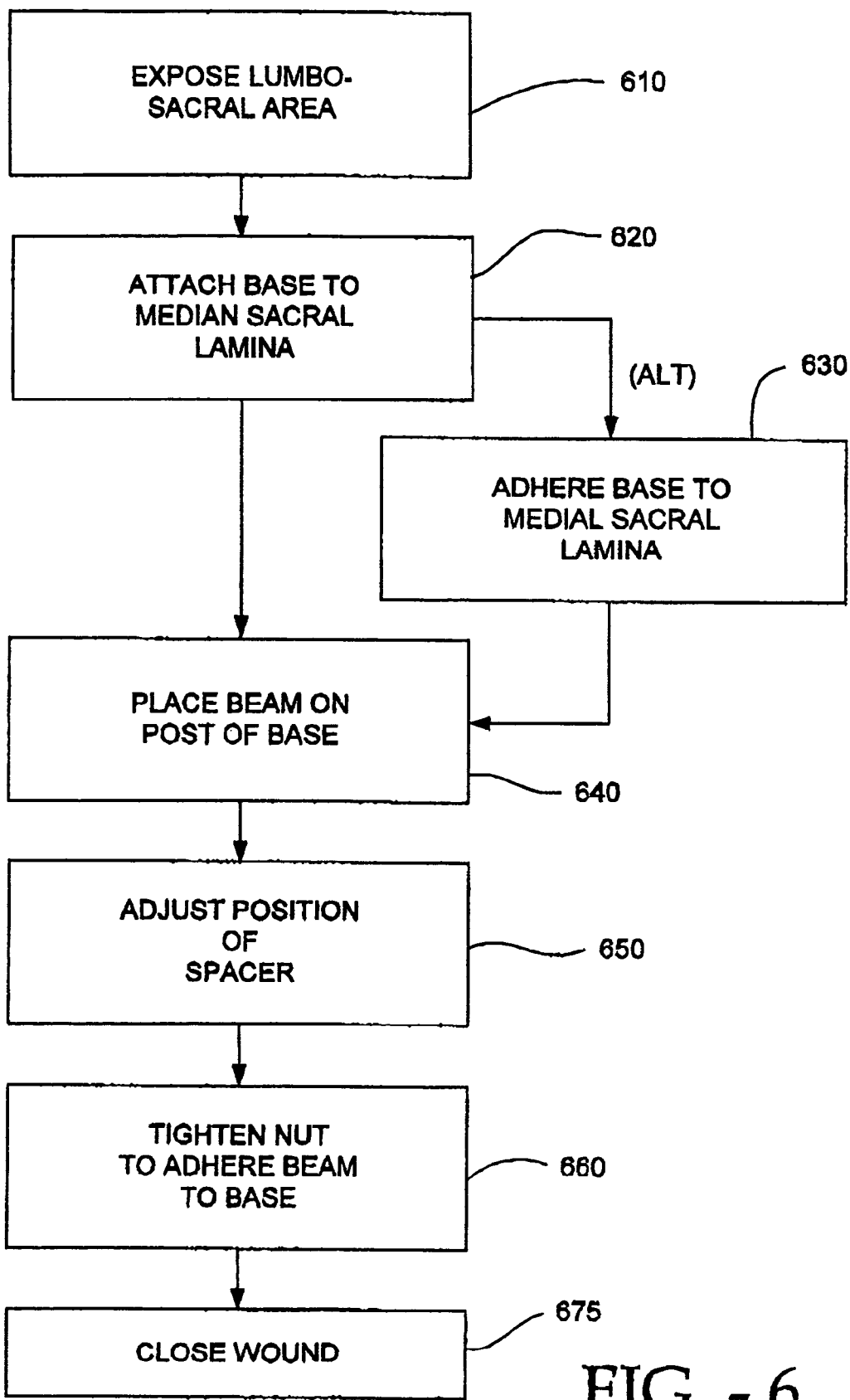
FIG. 6 is a block diagram of an embodiment of the method of implanting the implant between the S1 and L5 vertebrae.

FIG. 6 shows a block diagram of the steps of the method of implanting an implant of this invention. The first step involves exposing the lumbosacral area 610. After exposing the region, the base 110 of the implant 100 is implanted such that it engages the median sacral lamina 620. At this point, if desired, the base 110 can be adhered to the median sacral lamina 630 by screwing the base 110 to the lamina by installing screws through the apertures 234 provided in the flanges 230, 231 of the base 110. Alternatively, the base 110 can be snug fit to the lamina.

If not preassembled, at this point the beam 140 is placed on the base 110 by engaging the beam 140 with the post 222 via the aperture 342 of the beam 140 (step 640). The beam 140 can be moved in a first and/or second direction to place the spacer 142 in an optimum position with respect to the spinous process of the L5 vertebrae 650. Once the beam 140 spacer 142 assembly is positioned, the nut 160, or other adhering mechanism, is tightened to the post 222 to keep the beam 140 spacer 142 in position relative to the spinous process of the L5 vertebrae (step 660). If desired, a plurality of beams of different lengths or having differently shaped distal ends can be provided in a kit. During a surgical procedure, the doctor can select the beam with the length and the distal end shape that is appropriate for the anatomy of the patient. Thereafter, the wound is closed 670. Generally, the implant has been designed to be implanted without altering the L5 or S1 bone. The offset platform 224 and the slot 250 have been designed to accommodate the S1 form. However, due the configuration of the S1 bone, a small bone piece such as from the median sacral crest may need to be removed in order to accommodate the platform 224. The removal of this bone should not effect the stability of the bone structure as there is no bearing load from the implant 100 or the spine placed on the location where the bone is removed.

If at a later time it is determined that the location of the spacer 142 relative to the L5 spinous process needs to be changed, the nut 160 can be surgically removed (through, for example, a cannula) and the beam 140 and spacer 142 moved toward or away from the spinous process, as desired.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and its equivalence.

What is claimed:

1. An implant adapted to be placed between L5 and S1 vertebrae comprising:

a brace with a first end adapted to contact an inferior surface of a spinous process of the L5 vertebra, and a second end; and a base with a central platform and first and second lateral sections, the base having an anterior surface that faces towards the S1 vertebra and an opposing posterior surface that faces away from the S1 vertebra when the base is attached to the S1 vertebra, the base having at least one hook that extends outward from the anterior surface to engage the S1 vertebra;

an elongated connector that connects the brace to the platform;

the brace including a first surface that faces towards the base and a second surface that faces away from the base, a thickness of the brace measured between the first and second surfaces being greater at the first end than the second end with the first end being enlarged relative to the second end;

the brace and base being connected together by the connector with the brace positioned at the posterior surface of the base and the first end positioned to contact the inferior surface of the spinous process of the L5 vertebra during extension of the spine.

2. An implant adapted to be placed between vertebrae comprising:

a body;

at least one hook extending from the body and including a first contact surface that faces in an inferior direction to allow the body to engage a first vertebra;

a brace extending from the body and including a distal end with a second contact surface that faces in a superior direction and an elongated section extending outward from the distal end that is secured to the body, the distal end including a greater thickness than the elongated section; and a device that secures the elongated section to the body and positions the second contact surface to contact an inferior surface of a spinous process of a second vertebra positioned superior of the first vertebra during extension of the vertebrae;

the brace includes an elongated aperture and the device includes a post that extends through the aperture and can be secured to the aperture in a plurality of positions in order to position the brace relative to the body.

3. The implant of claim 2 wherein the second contact surface includes a convex surface that extends within a median plane of the implant.

4. The implant of claim 2 wherein the brace is positioned on a posterior side of the body when implanted, the second contact surface including a convex surface that is curved in an anterior-posterior direction.

5. The implant of claim 2 wherein:
at least part of the implant is comprised of a material selected from the group consisting of: polyethertherketone, polyaryletherketone, and polyetherketoneketone.

6. The implant of claim 2 wherein:
at least part of the implant is comprised of a material selected from the group consisting of polyetherketoneetherketoneketone, ployetheretherketoneketone, polyketone, and polyetherketone.

7. The implant of claim 2 wherein: at least part of the implant is comprised of titanium.

8. The implant of claim 2 wherein the device secures the brace to the body in a plurality of positions.

9. The implant of claim 2 wherein the distal end is bulbous.

10. The implant of claim 2 wherein the distal end is one of elliptical, ovoid, oval, and round.

11. The implant of claim 2 wherein the distal end provides a surface which is at an angle to the elongated section, which surface is adapted to engage a L5 vertebra.

12. The implant of claim 2 wherein the distal end provides a surface that is adapted to spread a contact load between a L5 vertebra and the distal end.

13. The implant of claim 2 wherein the distal end is adapted to engage a spinous process of a L5 vertebra.

14. The implant of claim 2 wherein the distal end is adapted to engage a spinous process of a L5 vertebra over a conforming contact area.

15. The implant of claim 2 wherein the distal end includes a convex surface that is adapted to engage a spinous process of a L5 vertebra in order to spread the load between the distal end and the spinous process of the L5 vertebra.

16. The implant of claim 2 wherein the body includes a first portion and second portion with a beam platform located between the first and second positions and the beam platform spaced from the first and second positions in order to space the brace from the first and second portions.

17. The implant of claim 16 wherein the hook extends from the first portion and another hook extends from the second portion.

18. The implant of claim 16 wherein the device extends from the platform.

19. The implant of claim 2 including a device configured to secure the base to an S1 vertebra.

20. An implant adapted to be placed between L5 and S1 vertebrae comprising:
a body having first and second portions with a platform located between the first and second portions, the platform attached to a posterior surface of the first and second portions, the body including a superior-most edge;

a notch formed by the body between medial edges of the first and second portions and an anterior surface of the platform, the notch being sized to extend over a midline of the S1 vertebra when the body is attached to the S1 vertebra;

first and second hooks extending from the first and second portions respectively, the first and second hooks being spaced apart to engage with the S1 vertebra on opposite lateral sides of the midline of the S1 vertebra;

a brace with a planar proximal end and a distal end having a curved surface, the brace attached to an opposite side of the platform from the notch; and a device that can selectively position the brace relative to the body in a plurality of positions to locate the curved surface of the distal end outward beyond the superior-most edge of the body to contact an inferior surface of a spinous process of the L5 vertebra.

21. The implant of claim 20 wherein the distal end includes a convex surface that extends in a median plane of the implant.

22. The implant of claim 20 wherein:
at least part of the implant is comprised of a material selected from the group consisting of: polyethertherketone, polyaryletherketone, and polyetherketoneketone.

23. The implant of claim 20 wherein:
at least part of the implant is comprised of a material selected from the group consisting of: polyetherketoneetherketoneketone, ployetheretherketoneketone, polyketone, and polyetherketone.

24. The implant of claim 20 wherein: at least part of the implant is comprised of titanium.

25. The implant of claim 20 wherein the device secures the brace to the body in a plurality of positions.

26. The implant of claim 20 wherein the distal end is bulbous.

27. The implant of claim 20 wherein the distal end is one of elliptical, ovoid, oval, and round.

28. The implant of claim 20 wherein the distal end provides a surface which is at an angle to the proximal end, which surface is adapted to engage the L5 vertebra.

29. The implant of claim 20 wherein the distal end provides a surface that is adapted to spread a contact load between the L5 vertebra and the distal end.

30. The implant of claim 20 wherein the distal end is adapted to engage the spinous process of the L5 vertebra.

31. The implant of claim 20 wherein the distal end is adapted to engage the spinous process of the L5 vertebra over a conforming contact area.

32. The implant of claim 20 wherein the distal end includes a convex surface that is adapted to engage the spinous process of the L5 vertebra in order to spread the load between the distal end and the spinous process of the L5 vertebra.

33. The implant of claim 20 wherein the proximal end includes an elongated aperture and the device extends through the aperture and can be secured to the aperture in a plurality of positions in order to position the brace relative to the body in a plurality of positions.

34. The implant of claim 20 wherein the device extends from the platform.

35. An implant adapted to be placed between vertebrae comprising;
   a body having first and second portions with a platform located between the first and second portions;
   a hook extending from an anterior side of the body and being adapted to engage a first vertebra;
   a brace connected to a posterior side of the body and including an elongated shape with a major axis, the brace including a first end on the major axis positioned to contact an inferior surface of a spinous process of a second vertebra when implanted; and
   a device that can selectively position the brace relative to the body, wherein the first end extends beyond the body such that a mid-point of the first end contacts against the spinous process of the second vertebra.

36. The implant of claim 35 wherein:
   at least part of the implant is comprised of a material selected from the group consisting of: polyethertherketone, polyaryletherketone, and polyetherketoneketone.

37. The implant of claim 35 wherein:
   at least part of the implant is comprised of a material selected from the group consisting of: polyetherketoneetherketoneketone, ployetheretherketoneketone, polyketone, and polyetherketone.

38. The implant of claim 35 wherein: at least part of the implant is comprised of titanium.

39. The implant of claim 35 wherein the device secures the brace to the body in a plurality of positions.

40. The implant of claim 35 wherein the first end is bulbous.

41. The implant of claim 35 wherein the first end is one of elliptical, ovoid, oval, and round.

42. The implant of claim 35 wherein the first end provides a surface that is adapted to spread a contact load between a L5 vertebra and the distal end.

43. The implant of claim 35 wherein the first end is adapted to engage a spinous process of a L5 vertebra.

44. The implant of claim 35 wherein the first end is adapted to engage a spinous process of a L5 vertebra over a conforming contact area.

45. The implant of claim 35 wherein the first end includes a convex surface that is adapted to engage a spinous process of a L5 vertebra in order to spread the load between the first end and the spinous process of a L5 vertebra.

46. An implant adapted to be placed between vertebrae comprising:
   a body;
   at least one hook extending from a first side of the body and adapted to allow the body to engage a first vertebra;
   a brace positioned on an opposite second side of the body and extending outward from the body; the brace having a distal end with a curved surface with a first thickness and a beam with a second smaller thickness, wherein the curved surface is adapted to contact an inferior surface of a spinous process of a second vertebra; and
   a device that connects the beam to the body to secure the brace to the body and positions the curved surface outward from the body to contact the inferior surface of the spinous process of the second vertebra during extension of the vertebrae, the device includes a post and a connector that attaches to the post and is able to position the curved surface at a variety of heights outward from the body.

* * * * *